US011040926B2

(12) United States Patent
Pandey et al.

(10) Patent No.: US 11,040,926 B2
(45) Date of Patent: Jun. 22, 2021

(54) INTEGRATED PROCESS FOR MAXIMIZING RECOVERY OF AROMATICS

(71) Applicant: UOP LLC, Des Plaines, IL (US)

(72) Inventors: Gautam Pandey, Gurgaon (IN); Krishna Mani, Gurgaon (IN); Deepak Bisht, New Delhi (IN); Priyesh Jayendrakumar Jani, Gurgaon (IN); Vikrant Vilasrao Dalal, Gurgaon (IN); Ram Ganesh Rokkam, Gurgaon (IN)

(73) Assignee: UOP LLC, Des Plaines, IL (US)

( * ) Notice: Subject to any disclaimer, the term of this patent is extended or adjusted under 35 U.S.C. 154(b) by 107 days.

(21) Appl. No.: 16/517,865

(22) Filed: Jul. 22, 2019

(65) Prior Publication Data

US 2021/0024434 A1 Jan. 28, 2021

(51) Int. Cl.
*C10G 7/00* (2006.01)
*C10G 35/04* (2006.01)
*C07B 63/02* (2006.01)
*C07C 15/08* (2006.01)
*C07C 15/04* (2006.01)

(52) U.S. Cl.
CPC .............. *C07B 63/02* (2013.01); *C07C 15/04* (2013.01); *C07C 15/08* (2013.01)

(58) Field of Classification Search
CPC .................................. C10G 7/00; C10G 35/04
See application file for complete search history.

(56) References Cited

U.S. PATENT DOCUMENTS

| | | | | |
|---|---|---|---|---|
| 3,945,913 A | * | 3/1976 | Brennan | ................ C10G 59/02 208/137 |
| 4,053,388 A | | 10/1977 | Bailey | |
| 4,078,990 A | * | 3/1978 | Brennan | ................... C07C 6/12 208/64 |
| 4,211,886 A | * | 7/1980 | Tabak | ....................... C07C 4/12 585/321 |
| 6,740,788 B1 | * | 5/2004 | Maher | ..................... C07C 6/126 585/319 |

FOREIGN PATENT DOCUMENTS

| | | |
|---|---|---|
| CN | 106190289 A | 12/2016 |
| CN | 206014783 U | 3/2017 |
| CN | 106588540 A | 4/2017 |
| FR | 2401125 A1 | 3/1979 |

* cited by examiner

*Primary Examiner* — Randy Boyer
(74) *Attorney, Agent, or Firm* — Paschall & Associates, LLC; James C. Paschall

(57) ABSTRACT

An integrated process for maximizing recovery of aromatics is provided. The process comprises passing at least a portion of a xylene column bottoms stream to a heavy aromatics column to provide a heavy aromatics column bottoms stream comprising $C_{9+}$ aromatics and a heavy aromatics column overhead stream. The heavy aromatics column bottoms stream is passed to a second stage hydrocracking reactor of a two-stage hydrocracking reactor. In the second stage hydrocracking reactor, the heavy aromatics column bottoms stream is hydrocracked in the presence of a hydrocracking catalyst and hydrogen to provide a hydrocracked effluent stream.

20 Claims, 2 Drawing Sheets

INTEGRATED PROCESS FOR MAXIMIZING RECOVERY OF AROMATICS

FIELD

The field relates to an integrated process for maximizing recovery of aromatics. More particularly, the field relates to integration of various processes for maximizing recovery of aromatics.

BACKGROUND

Basic petrochemical intermediates such as benzene, toluene and xylenes ("BTX") find wide and varied application in chemical synthesis. These intermediates are obtained from a hydrocarbon feed, using a combination of processes to form and recover these intermediates. Therefore, various process units are combined in an aromatic complex to produce basic petrochemical intermediates. However, production of basic petrochemical intermediates from the aromatic complex depends not only on the efficient conversion of the hydrocarbon feed through various process units to produce basic petrochemical intermediates, but also on capital costs and energy costs involved in installing various process units of the aromatic complex.

The aromatic complexes can have varied configuration depending upon the circumstances. A typical aromatic complex includes hydrotreating, catalytic reforming, and aromatics extraction. Hydrotreating removes sulfur, nitrogen and other contaminants present in the hydrocarbon feed. Catalytic reforming produces aromatics from the hydrocarbon feed. Aromatics extraction is used for the extraction of BTX. Typically, a reformate stream is obtained from the reforming unit. Therefrom, xylenes are recovered from the reformate stream. Generally, a residue stream comprising heavy aromatics is obtained after xylene separation from the reformate stream.

The residue stream comprising heavy aromatics, usually, is separated into a vapor stream and a liquid stream. Conventionally, the liquid stream is removed from the aromatic complex. The liquid stream is sent to fuel oil pool/fuel oil blending without further recovery of aromatics. Since an aromatic complex includes various units for petrochemical intermediates, refiners strive to maximize recovery of hydrocarbons from the aromatic complex thereby optimizing cost and operational expenditures for the aromatic complex.

Accordingly, it is desirable to provide new apparatuses and processes for providing cost benefits in terms of lower capital and operational expenditures. Also, there is a need for an alternative approach to maximizing recovery of hydrocarbons from a heavy aromatics stream obtained from the aromatic complex. Other desirable features and characteristics of the present subject matter will become apparent from the subsequent detailed description of the subject matter and the appended claims, taken in conjunction with the accompanying drawings and this background of the subject matter.

BRIEF SUMMARY

Various embodiments contemplated herein relate to processes and apparatuses for maximizing recovery of aromatics. The exemplary embodiments taught herein provide an integrated process for maximizing recovery of aromatics by integrating various processes.

In accordance with an exemplary embodiment, an integrated process is provided for maximizing the recovery of aromatics. The process comprises passing at least a portion of a xylene column bottoms stream to a heavy aromatics column to provide a heavy aromatics column bottoms stream comprising $C_{9+}$ aromatics and a heavy aromatics column overhead stream. The heavy aromatics column bottoms stream may be hydrocracked in a second stage hydrocracking reactor of a two-stage hydrocracking reactor in the presence of a hydrocracking catalyst and hydrogen to provide a hydrocracked effluent stream. In accordance with another exemplary embodiment, the heavy aromatics column bottoms stream may be hydrocracked in the second stage hydrocracking reactor in the presence of a second stage hydrocracking catalyst and hydrogen to provide a second stage hydrocracked effluent stream. A hydrocarbonaceous feed may be hydrocracked in a first stage hydrocracking reactor in the presence of a first stage hydrocracking catalyst and hydrogen to provide a first stage hydrocracked effluent stream. The second stage hydrocracked effluent stream and the first stage hydrocracked effluent stream may be fractionated to provide a bottoms stream comprising unconverted oil (UCO). The bottoms stream comprising UCO may be passed to the second stage hydrocracking reactor.

The integrated process of the present disclosure envisages integration of an aromatic complex with a hydrocracking unit. The integrated process envisages passing the heavy aromatics column bottoms stream from the aromatic complex to the hydrocracking unit to maximize recovery of aromatics. Applicants have found that passing the heavy aromatics column bottoms stream from the aromatic complex to the hydrocracking unit increases the recovery of aromatics from the heavy aromatics column bottoms stream. The hydrocracking conditions in the hydrocracking unit promote ring opening and cleaving of alkyl side chains. This will result in a conversion of low value $C_{9+}$ aromatics present in the heavy aromatics column bottoms stream to high value aromatics such as $C_6$'s to $C_8$'s. Applicants have found that a comparative lower operating pressure of the hydrocracking unit will prohibit aromatics saturation. Therefore, the integrated process of the present disclosure provides integration of the aromatic complex with a hydrocracking unit to maximize recovery of aromatics.

These and other features, aspects, and advantages of the present invention will become better understood upon consideration of the following detailed description, drawings and appended claims.

BRIEF DESCRIPTION OF THE DRAWING

The various embodiments will hereinafter be described in conjunction with the following FIGURES, wherein like numerals denote like elements.

DEFINITIONS

Figure 1:
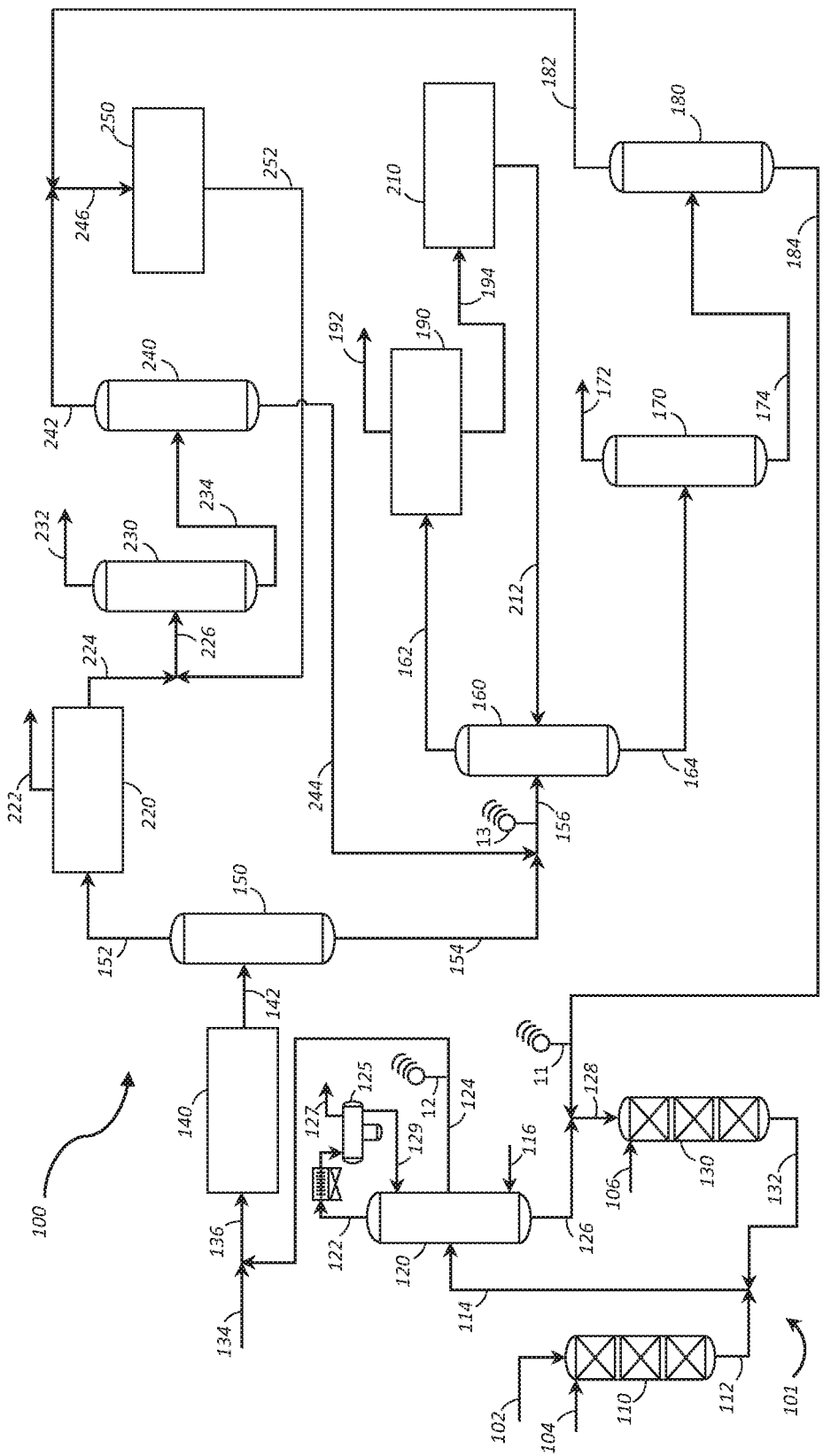
FIG. 1 is a schematic diagram of an integrated process and an apparatus for maximizing recovery of aromatics in accordance with an exemplary embodiment.

As used herein, the term "column" means a distillation column or columns for separating one or more components of different volatilities. Unless otherwise indicated, each column includes a condenser on an overhead of the column to condense the overhead vapor and reflux a portion of an overhead stream back to the top of the column. Also included is a reboiler at a bottom of the column to vaporize and send a portion of a bottom stream back to the bottom of the column to supply fractionation energy. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column. Alternatively, a stripping stream may be used for heat input at the bottom of the column.

As used herein, the term "stream" can include various hydrocarbon molecules and other substances.

As used herein, the term "overhead stream" can mean a stream withdrawn in a line extending from or near a top of a vessel, such as a column.

As used herein, the term "bottoms stream" can mean a stream withdrawn in a line extending from or near a bottom of a vessel, such as a column.

The term "$C_{x-}$" wherein "x" is an integer means a hydrocarbon stream with hydrocarbons have x and/or less carbon atoms and preferably x and less carbon atoms.

The term "$C_{x+}$" wherein "x" is an integer means a hydrocarbon stream with hydrocarbons have x and/or more carbon atoms and preferably x and more carbon atoms.

As used herein, the term "passing" includes "feeding" and "charging" and means that the material passes from a conduit or vessel to an object.

As used herein, the term "portion" means an amount or part taken or separated from a main stream without any change in the composition as compared to the main stream. Further, it also includes splitting the taken or separated portion into multiple portions where each portion retains the same composition as compared to the main stream.

As used herein, the term "unit" can refer to an area including one or more equipment items and/or one or more sub-units. Equipment items can include one or more reactors or reactor vessels, heaters, separators, drums, exchangers, pipes, pumps, compressors, and controllers. Additionally, an equipment item, such as a reactor, dryer, or vessel, can further include one or more units or sub-units.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description. The Figures have been simplified by the deletion of a large number of apparatuses customarily employed in a process of this nature, such as vessel internals, temperature and pressure controls systems, flow control valves, recycle pumps, etc. which are not specifically required to illustrate the performance of the invention. Furthermore, the illustration of the process of this invention in the embodiment of a specific drawing is not intended to limit the invention to specific embodiments set out herein.

As depicted, process flow lines in the figures can be referred to, interchangeably, as, e.g., lines, pipes, branches, distributors, streams, effluents, feeds, products, portions, catalysts, withdrawals, recycles, suctions, discharges, and caustics.

An integrated process for maximizing recovery of aromatics is addressed with reference to a process and an apparatus 100 according to an embodiment as shown in FIG. 1. Referring to FIG. 1, the process and apparatus 100 comprise a hydrocracking unit 101, a reforming unit 140, a reformate splitter 150, a xylene column 160, a heavy aromatics column 180, a paraxylene separation unit 190 and an isomerization unit 210. In an exemplary embodiment, the hydrocracking unit 101 may comprise a two-stage hydrocracking reactor. As shown in FIG. 1, a hydrocarbonaceous feed in line 102 is provided to a first stage hydrocracking reactor 110. A hydrogen gas stream in line 104 may also be provided to the first stage hydrocracking reactor 110. In an alternate scheme, the hydrogen gas stream in line 104 may be combined with the hydrocarbonaceous feed in line 102 and the combined stream may be passed to the first stage hydrocracking reactor 110. The hydrocarbonaceous feed may be hydrocracked in the first stage hydrocracking reactor 110 in the presence of a first stage hydrocracking catalyst and hydrogen to provide a first stage hydrocracked effluent stream in line 112. In an exemplary embodiment, the first hydrocarbonaceous feed may comprise one or more of vacuum gas oil (VGO), diesel, light cycle oil (LCO), heavy thermally cracked gas oil, kerosene, vacuum residue, and deasphalted oil (DAO).

As shown, each stage of the two-stage hydrocracking reactor 101 may comprise one or more beds adaptable to contain the hydrocracking catalyst. Suitable hydrocracking catalysts that can be used as the first stage hydrocracking catalyst may comprise catalysts that utilize amorphous silica-alumina bases or low-level zeolite bases combined with one or more Group VIII or Group VIB metal hydrogenating components. The zeolite cracking bases are sometimes referred to in the art as molecular sieves and are usually composed of silica, alumina and one or more exchangeable cations such as sodium, magnesium, calcium, rare earth metals, etc. The active metals that may be employed in hydrocracking catalysts as hydrogenation components are those of Group VIII, i.e., iron, cobalt, nickel, ruthenium, rhodium, palladium, osmium, iridium and platinum. In addition to these metals, other promoters may also be employed in conjunction therewith, including the metals of Group VIB, e.g., molybdenum and tungsten.

The hydrocracking conditions of the first stage hydrocracking reactor 110 may include a temperature from about 290° C. (550° F.) to about 468° C. (875° F.), or from about 343° C. (650° F.) to about 445° C. (833° F.), a pressure from about 4800 kPa (gauge) (700 psig) to about 11000 kPa (gauge) (1600 psig), and a liquid hourly space velocity (LHSV) from about 0.4 hr$^{-1}$ to about 2.5 hr$^{-1}$.

The first stage hydrocracked effluent stream in line 112 may be passed to a fractionation column 120 in line 114. A second stage hydrocracked effluent stream in line 132 may also be passed to the fractionation column 120 in line 114. A suitable stripping media in line 116 may also be passed into the fractionation column 120. Preferably, steam is used as stripping media in line 116. In the fractionation column 120, the first stage hydrocracked effluent stream and the second stage hydrocracked effluent stream may be separated into an overhead stream in line 122 and a bottoms stream comprising unconverted oil in line 126 or an unconverted oil stream in line 126. Optionally, another stream in line 124 may also be taken from a side of the fractionation column 120. The overhead stream in line 122 may be condensed in a condenser and perhaps cooled in a cooler before it enters an overhead receiver 125 in downstream communication with the fractionation column 120. The use of cooler is optional and the overhead stream in line 122 may be passed to the overhead receiver 125 without cooling. In the receiver 125, the overhead stream in line 122 may be separated to provide a receiver overhead vapor stream comprising $C_6$– hydrocarbons in line 127 and a receiver overhead liquid stream in line 129. The receiver overhead liquid stream in line 129 may be refluxed to the fractionation column 120.

Although not shown in FIG. 1, the first stage hydrocracked effluent stream in line 112 and the second stage hydrocracked effluent stream in line 132 may be passed to a separation unit before being passed to the fractionation column 120. The separation unit may comprise a hot separator and a cold separator and corresponding flash drums to facilitate the separation, reduce pressure and cool the hydrocracked effluent stream. Accordingly, the first stage hydrocracked effluent stream in line 112 and the second stage hydrocracked effluent stream in line 132 may be passed to the separators and thereafter to corresponding flash drum before these streams are passed to the fractionation column 120. The separated liquid streams may also be passed to a stripping column, also not shown, to remove vapors before passing to the fractionation column 120.

The bottoms stream comprising unconverted oil in line 126 may be passed to a second stage hydrocracking reactor 130. As described hereinafter in detail, a heavy aromatics column bottoms stream comprising $C_{9+}$ aromatics in line 184 may also be passed to the second stage hydrocracking reactor 130. In an exemplary embodiment, the heavy aromatics column bottoms stream comprising $C_{9+}$ aromatics in line 184 may be combined with the bottoms stream comprising unconverted oil in line 126 to provide a combined stream in line 128. The combined stream in line 128 may be passed to the second stage hydrocracking reactor 130. As shown in FIG. 1, a hydrogen stream in line 106 may also be passed to the second stage hydrocracking reactor 130. The bottoms stream comprising unconverted oil 126 and the heavy aromatics column bottoms stream comprising $C_{9+}$ aromatics 184 may be hydrocracked in the second stage hydrocracking reactor 130 in the presence of a second stage hydrocracking catalyst and hydrogen to provide a second stage hydrocracked effluent stream in line 132. The second stage hydrocracked effluent stream in line 132 may be passed to the fractionation column 120. In an exemplary embodiment, the second stage hydrocracked effluent stream in line 132 may be combined with the first stage hydrocracked effluent stream in line 112. A combined stream in line 114 may be passed to the fractionation column 120. In another exemplary embodiment, the second stage hydrocracked effluent stream in line 132 and the first stage hydrocracked effluent stream in line 112 may be passed separately to the fractionation column 120.

The second stage hydrocracking reactor 130 may comprise one or more beds adaptable to contain the hydrocracking catalyst. Suitable hydrocracking catalysts that can be used as the second stage hydrocracking catalyst may comprise catalysts that utilize amorphous silica-alumina bases or low-level zeolite bases combined with one or more Group VIII or Group VIB metal hydrogenating components. The zeolite cracking bases are sometimes referred to in the art as molecular sieves and are usually composed of silica, alumina and one or more exchangeable cations such as sodium, magnesium, calcium, rare earth metals, etc. The active metals that may be employed in preferred hydrocracking catalysts as hydrogenation components are those of Group VIII, i.e., iron, cobalt, nickel, ruthenium, rhodium, palladium, osmium, iridium and platinum. In addition to these metals, other promoters may also be employed in conjunction therewith, including the metals of Group VIB, e.g., molybdenum and tungsten. The second stage hydrocracking catalyst may be the same or different that the first stage hydrocracking catalyst. In another exemplary embodiment, the heavy aromatics column bottoms stream 184 may be passed in between the one or more beds of the second stage hydrocracking catalyst.

The hydrocracking conditions of the second stage hydrocracking reactor 130 may include a temperature from about 290° C. (550° F.) to about 468° C. (875° F.), or from about 343° C. (650° F.) to about 445° C. (833° F.), a pressure from about 4800 kPa (gauge) (700 psig) to about 11000 kPa (gauge) (1600 psig), and a liquid hourly space velocity (LHSV) from about 0.4 hr$^{-1}$ to about 2.5 hr$^{-1}$.

The integrated process of the present disclosure provides an integration of a hydrocracking process/unit with an aromatic complex. A bottoms stream obtained from the heavy aromatics column of the aromatic complex usually comprises $C_{9+}$ aromatics. In a typical aromatic complex, the heavy aromatics column bottoms stream rich in $C_{9+}$ aromatics is sent to gasoline or fuel oil blending. The applicants have found that instead of passing the heavy aromatics column bottoms stream to gasoline or fuel oil blending, the heavy aromatics column bottoms stream can be passed to a hydrocracking unit to maximize the recovery of aromatics. The present integrated process, by passing the heavy aromatics column bottoms stream to the second stage hydrocracking reactor, which may be operating at a comparatively lower pressure for naphtha maximization, also inhibits the aromatics saturation of the heavy aromatics column bottoms stream. Therefore, in such a way the present scheme maximizes recovery of aromatics by integrating the hydrocracking process/unit with the aromatic complex.

As shown in FIG. 1, a naphtha feed stream in line 134 may be passed to a reforming unit 140 of the aromatic complex. A heavy naphtha stream in line 124, taken from the fractionation column 120, may also be passed to the reforming unit 140. In an exemplary embodiment, the heavy naphtha stream in line 124 may be withdrawn as a side stream or another stream from the fractionation column 120. In another exemplary embodiment, the naphtha feed stream in line 134 may be combined with the heavy naphtha stream in line 124 to provide a combined stream in line 136. The combined stream in line 136 may be passed to the reforming unit 140. In an alternate scheme, the naphtha feed stream in line 134 and the heavy naphtha stream in line 124 may be passed separately to the reforming unit 140. The reforming unit 140 may be operated at a pressure of from about 101.325 kPa (absolute) (14.7 psia) to 6080 kPa (absolute) (882 psia), or from about 101.325 kPa (absolute) (14.7 psia) to about 2030 kPa (absolute) (294 psia), a temperature from about 260° C. (500° F.) to about 560° C. (1040° F.). In the reforming unit 140, the naphtha feed stream in line 134 and the heavy naphtha stream in line 124 may be reformed in a reforming reactor in the presence of hydrogen and a reforming catalyst to provide a reformate effluent stream in line 142. In the reforming unit 140, reforming reactions take place in a reforming reactor. The primary reforming reactions convert paraffins and naphthenes through dehydrogenation and cyclization to aromatics. The dehydrogenation of paraffins may yield olefins, and the dehydrocyclization of paraffins and olefins may yield aromatics. The reforming process is an endothermic process, and to maintain the reaction, the reforming reactor may comprise a catalytic reactor that may comprise a plurality of catalytic reactors with one or more interreactor heaters.

Reforming catalysts generally comprise a metal on a support. The support can include a porous material, such as an inorganic oxide or a molecular sieve, and a binder. Inorganic oxides used for support include, but are not limited to, alumina, magnesia, titania, zirconia, chromia, zinc oxide, thoria, boria, ceramic, porcelain, bauxite, silica, silica-alumina, silicon carbide, clays, crystalline zeolitic aluminasilicates, and mixtures thereof. Reforming catalysts may comprise one or more Group VIII noble metals. In an exemplary embodiment, the reforming catalyst may comprise one or more of a noble metals selected from platinum, palladium, rhodium, ruthenium, osmium, and iridium. The catalyst can also include a promoter element from Group IIIA or Group IVA. These metals include gallium, germanium, indium, tin, thallium and lead.

The reformate effluent stream in line 142 may be passed to a reformate splitter 150. In an embodiment, the reformate splitter 150 may include a fractionation column. In the reformate splitter 150, the reformate effluent stream in line 142 may be split to provide a reformate splitter overhead stream in line 152 and a reformate splitter bottoms stream in line 154. In an exemplary embodiment, the reformate splitter overhead stream in line 152 may comprise $C_{7-}$ hydrocarbons and the reformate splitter bottoms stream in line 154 may comprise $C_{8+}$ aromatics.

In an exemplary embodiment, the reformate splitter bottoms stream in line 154 may be passed to a xylene column 160. If needed, the reformate splitter bottoms stream in line 154 may be clay treated to saturate or selectively saturate olefins or diolefins present in the reformate splitter bottoms stream in line 154. The concentration of olefins in the reformate feed to the saturation zone depends on reforming feedstock, severity and reforming operating conditions and generally ranges from about 0.2 to about 3 mass %. The clay treatment may selectively hydrogenate about 50%, or about 70%, or 80% or more of the olefins or diolefins present in the reformate splitter bottoms stream in line 154. The treated reformate splitter bottoms stream may be sent to the xylene column 160 for xylene recovery. However, clay treatment is optional and the reformate splitter bottoms stream in line 154 may be passed to the xylene column 160 without clay treatment.

As described herein after in detail, a toluene column bottoms stream in line 244 and an isomerized effluent stream in line 212 may also be passed to the xylene column 160 along with the reformate splitter bottoms stream in line 154. These streams may be combined in any suitable manner or passed separately to the xylene column 160. In another exemplary embodiment, the reformate splitter bottoms stream in line 154 and the toluene column bottoms stream in line 244 may be combined to provide a combined stream in line 156. The combined stream in line 156 may be passed to the xylene column 160. In the xylene column 160, xylene may be separated from the reformate splitter bottoms stream in line 154, the toluene column bottoms stream in line 244, and the isomerized effluent stream in line 212 to provide a xylene column overhead stream comprising a mixture of xylenes in line 162 and a xylene column bottoms stream in line 164.

The xylene column overhead stream in line 162 may be passed directly to a paraxylene separation unit 190. In the paraxylene separation unit 190, a paraxylene stream may be separated in line 192 from the mixture of xylenes in the xylene column overhead stream 162. Adsorptive separation or any efficient method may be employed in the paraxylene separation unit 190 to separate the paraxylene stream from the other xylenes. A paraxylene lean stream in line 194 may be withdrawn from the paraxylene separation unit 190. The paraxylene lean stream in line 194 may be depleted of paraxylene to a level of less than 1 wt %. The paraxylene lean stream in line 194 may be passed to an isomerization unit 210 to provide an isomerized effluent stream in line 212.

The isomerization unit 210 may include an isomerization reactor having one or more beds of isomerization catalyst for isomerizing the paraxylene lean stream to have an increased concentration of paraxylene. Additional paraxylene may be produced in the isomerization unit 210 by reestablishing an equilibrium distribution of xylene isomers. Any ethylbenzene in the paraxylene lean stream in line 194 may be either converted to additional xylenes or dealkylated to benzene, depending on the catalyst used in the isomerization unit 210. The isomerized effluent stream in line 212 may be recycled back to the xylene column 160 for further separation of the paraxylene.

Typical isomerization catalysts contain a catalytically effective amount of molecular sieve and a catalytically effective amount of one or more hydrogenation metal components. Examples of suitable molecular sieves include MFI, MEL, EUO, FER, MFS, MTT, MTW, TON, MOR, UZM-8 and FAU types of zeolites. Pentasil zeolites such as MFI, MEL, MTW and TON are preferred, and MFI-type zeolites, such as ZSM-5, silicalite, Borolite C, TS-1, TSZ, ZSM-12, SSZ-25, PSH-3, and ITQ-1 are especially preferred. The catalysts may contain hydrogenation metal components and may contain suitable binder or matrix material such as inorganic oxides and other suitable materials. A refractory binder or matrix is typically used to facilitate fabrication of the isomerization catalyst, provide strength and reduce fabrication costs. The binder should be uniform in composition and relatively refractory to the conditions used in the process. In an exemplary embodiment, binder may include inorganic oxides such as one or more of alumina, aluminum phosphate, magnesia, zirconia, chromia, titania, boria and silica.

The aromatic complex may include an ortho-xylene column for the separation of ortho-xylene. In an exemplary embodiment, the xylene column bottoms stream in line 164 may be passed to an ortho-xylene column 170. In the ortho-xylene column 170, ortho-xylene may be recovered in an overhead stream in line 172. An ortho-xylene column bottoms stream in line 174 may be withdrawn from the ortho-xylene column 170. The ortho-xylene column bottoms stream in line 174 may comprise $C_{9+}$ aromatics. The ortho-xylene column bottoms stream in line 174 may be passed to the heavy aromatics column 180. In the heavy aromatics column 180, $C_{9+}$ aromatics may be separated in the heavy aromatics column bottoms stream in line 184. A heavy aromatics column overhead stream in line 182 may also be separated from the heavy aromatics column 180. The heavy aromatics column overhead stream in line 182 may comprise $C_{9-}$ aromatics.

The heavy aromatics column 180 is used to separate $C_{9+}$ aromatics from the xylene column bottoms stream in line 164 or the ortho-xylene column bottoms stream in line 174. In an exemplary embodiment, the heavy aromatics column 180 may be a de-heptanizer column. Although not shown in FIGURE, the heavy aromatics column 180 may have an overhead condenser and a receiver wherein the heavy aromatics column overhead stream in line 182 may be split into vapor and liquid streams. The overhead vapor stream from the receiver may be separated and passed to a fuel gas system. The overhead liquid stream from the receiver may be recycled to a transalkylation unit 250 in line 182.

In a typical aromatic complex, the bottoms stream in line 174 is separated and blended into fuel oil perhaps in the fuel oil pool. Applicants have found that the heavy aromatics column bottoms stream in line 184 may be integrated with the hydrocracking unit 101 to maximize the recovery of aromatics. The heavy aromatics column bottoms stream in line 184 may be passed to a last stage hydrocracking reactor of the hydrocracking unit 101 in order to maximize the recovery of aromatics. Applicants have found that the operating conditions in the hydrocracking unit 101 promote ring opening and cleaving of alkyl side chains for the hydrocarbons present in the heavy aromatics column bottoms stream. Passing the heavy aromatics column bottoms stream 184 to the second stage or the last stage hydrocracking reactor of the hydrocracking unit 101 results in a conversion of the $C_{9+}$ aromatics to a high value $C_6$, $C_7$, and $C_8$ aromatics and isomerized $C_5$ and $C_6$ aliphatics. Also, the hydrocracking unit 101 may be operated at a lower operating pressure for naphtha maximization. Applicants have found that such lower operating pressure inhibits aromatics saturation of the aromatics present in the heavy aromatics column bottoms stream 184. Such inhibition of aromatics saturation can be beneficial for integrating the aromatic complex with the hydrocracking unit 101. In this way, integrating the hydrocracking unit 101 with the aromatic complex via heavy aromatics column bottoms stream in line 184 may further maximize the overall aromatics recovery of the process.

Turning back to the reformate splitter 150, the reformate splitter overhead stream in line 152 may be passed to an extraction unit 220. In the extraction unit 220, aromatics may be recovered by separating paraffins from the reformate splitter overhead stream 152. Any suitable technique or process may be used for the separating the paraffins from the reformate splitter overhead stream in line 152 such as by solvent extraction. The paraffins may be separated into a raffinate stream in line 222. A benzene rich extract stream in line 224 may be removed from the extraction unit 220. The benzene rich extract stream in line 224 may be further processed for the recovery of benzene and toluene. As shown, the benzene rich extract stream in line 224 may be passed to a benzene column 230 to recover benzene. A transalkylated effluent stream in line 252 may also be passed to the benzene column 230. In an exemplary embodiment, the transalkylated effluent stream in line 252 may be combined with the benzene rich extract stream in line 224. A combined stream in line 226 may be passed to the benzene column 230. In an alternate scheme, the transalkylated effluent stream in line 252 and the benzene rich extract stream in line 224 may be passed separately to the benzene column 230. From the benzene column 230, benzene may be separated and recovered in an overhead stream in line 232. A benzene column bottoms stream in line 234 may be withdrawn and passed to a toluene column 240. In the toluene column 240, toluene may be separated to provide a toluene-rich overhead stream in line 242 and a toluene column bottoms stream in line 244 which may be passed to the xylene column 160. The toluene-rich overhead stream in line 242 may be passed to the transalkylation unit 250 for the production of additional xylenes and benzene. The heavy aromatics column overhead stream in line 182 may also be passed to the transalkylation unit 250 for further producing xylenes and benzene. The heavy aromatics column overhead stream in line 182 and the toluene rich overhead stream in line 242 may be combined to provide a combined stream in line 246. The combined stream in line 246 may be passed to the transalkylation unit 250. Alternately, the heavy aromatics column overhead stream in line 182 and the toluene rich overhead stream in line 242 may be passed separately to the transalkylation unit 250. In the transalkylation unit 250, the toluene rich overhead stream in line 242 and the heavy aromatics column overhead stream in line 182 may be transalkylated in the presence of a transalkylation catalyst to produce more xylenes in a transalkylated effluent stream in line 252. The transalkylated effluent stream in line 252 may be recycled back to the benzene column 230 for further recovery of xylenes.

Transalkylation catalysts that may be used in the transalkylation unit 250 are based on a solid-acid material combined with a metal component. Suitable solid-acid materials include all forms and types of mordenite, mazzite (omega zeolite), beta zeolite, ZSM-11, ZSM-12, ZSM-22, ZSM-23, MFI type zeolite, NES type zeolite, EU-1, MAPO-36, MAPSO-31, SAPO-5, SAPO-11, SAPO-41, silica-alumina mixtures thereof or ion exchanged versions of such solid-acids. Refractory inorganic oxides combined with the above-mentioned catalysts are usually found useful in a transalkylation process. A refractory binder or matrix is optionally utilized to facilitate fabrication of the catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, phosphate, zinc oxide and silica. In an exemplary embodiment, alumina may be used as binder. The catalyst may optionally contain additional modifier metal components. Modifier components of the catalyst may include, for example, tin, germanium, lead, indium, platinum, palladium and mixtures thereof.

Figure 2:
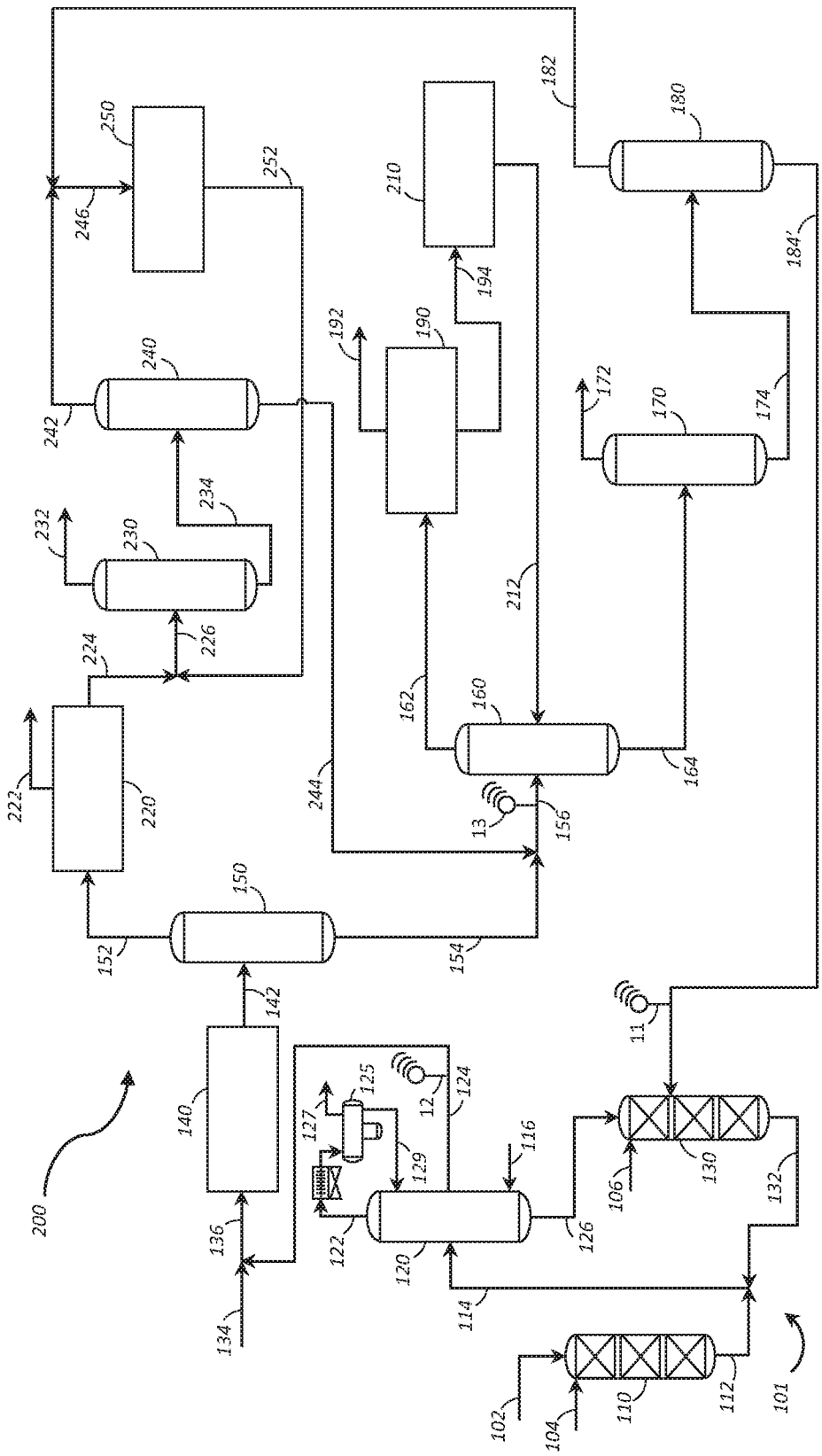
FIG. 2 is a schematic diagram of an integrated process and an apparatus for maximizing recovery of aromatics in accordance with another exemplary embodiment.

Turning now to FIG. 2, another exemplary embodiment of the integrated process for maximizing recovery of aromatics is addressed with reference to a process and apparatus 200. Many of the elements in the FIG. 2 have the same configuration as in FIG. 1 and bear the same respective reference number and have similar operating conditions. Elements in FIG. 2 that correspond to elements in FIG. 1 but have a different configuration bear the same reference numeral as in FIG. 1 but are marked with a prime symbol ('). The apparatus and process in FIG. 2 are configured and operated the same as in FIG. 1 with the exception of the noted following differences.

The bottoms stream comprising unconverted oil in line 126 or the unconverted oil stream in line 126 may be passed to the second stage hydrocracking reactor 130. In an exemplary embodiment, the second stage hydrocracking reactor 130 may comprise one or more beds adaptable to contain the second stage hydrocracking catalyst. Although FIG. 2 shows that the second stage hydrocracking reactor 130 comprises three beds of the second stage hydrocracking catalyst, the second stage hydrocracking reactor 130 may comprise more or less than three beds of the second stage hydrocracking catalyst.

The bottoms stream comprising unconverted oil in line 126 may be passed to the top bed of the second stage hydrocracking catalyst of the second stage hydrocracking reactor 130. As shown, a heavy aromatics column bottoms stream comprising $C_{9+}$ aromatics in line 184' may be passed to an interbed location between the second stage hydrocracking catalyst beds of the second stage hydrocracking reactor 130. The hydrogen stream in line 106 may also be passed to the second stage hydrocracking reactor 130. In an alternate scheme, the hydrogen stream in line 106 may be combined with the bottoms stream comprising unconverted oil in line 126. The combined stream may be passed to the second stage hydrocracking reactor 130. A reaction effluent from the top bed may be contacted with the heavy aromatics column bottoms stream in line 184'. The heavy aromatics column bottoms stream in line 184' may also work as a quench stream for the reaction effluent coming through the top bed. Further, the heavy aromatics column bottoms stream comprising $C_{9+}$ aromatics in line 184' may be separated into a plurality of heavy aromatics column bottoms streams wherein a first heavy aromatics column bottoms stream may be sent to a top bed of the second stage hydrocracking catalyst beds. The remaining streams may be passed to interbed locations located in between the downstream second stage hydrocracking catalyst beds of the second stage hydrocracking reactor 130 for serving as effluent quench and maximizing the recovery of aromatics in the second stage hydrocracking reactor 130. The rest of the process is same as described above for FIG. 1. Passing the heavy aromatics column bottoms stream in line 184 in between the hydrocracking catalyst beds of the second stage hydrocracking reactor 130 also improves the selectivity to high value aromatics such as $C_6$'s to $C_8$'s.

Usually, the heavy aromatics column bottoms stream from the aromatic complex is passed to fuel oil pool for fuel oil blending. Before passing and/or blending with the fuel oil pool, the heavy aromatics column bottoms stream requires further treatment to make it suitable for blending. However, the current process integrates the aromatic complex via the heavy aromatics column bottoms stream in line 184 with the hydrocracking unit 101 to maximize the conversion of $C_{9+}$ aromatics to high value aromatics such as $C_6$'s to $C_8$'s which may be passed to the gasoline pool. Also, the heavy aromatics column bottoms stream in line 184 does not need to undergo further treatment prior to charging the hydrocracking unit 101.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect. Further, the figure shows one or more exemplary sensors such as 11, 12, and 13, located on one or more conduits. Nevertheless, there may be sensors present on every stream so that the corresponding parameter(s) can be controlled accordingly.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

EXAMPLE

A process simulation example was performed to demonstrate the maximization of recovery of aromatics. 100 g of a heavy aromatics column bottoms stream was used for the second stage hydrocracking reactor of the hydrocracking unit. The simulation results are shown in the Table below:

TABLE

| Heavy Aromatics Column Bottoms Stream, g | $C_1$-$C_4$ Hydrocarbons, g | Hydrocracked Naphtha, g | Second Stage Hydrocracked Effluent, g | Reformate $C_6$-$C_8$ aromatics, g |
|---|---|---|---|---|
| 100 | 7.5 | 42.5 | 50 | 24.7 |

As shown in the Table, when 100 g of the heavy aromatics column bottoms stream were passed to the second stage hydrocracking reactor of the hydrocracking unit, 7.5 g of $C_1$-$C_4$ hydrocarbons, 42.5 g hydrocracked naphtha, and 50 g of UCO was produced. The 42.5 g of hydrocracked naphtha produced 24.7 g of $C_6$-$C_8$ aromatics in the reformate effluent stream.

Applicants have found that passing a 100 g of the heavy aromatics column bottoms stream in line 184 from the aromatics complex unit to the second stage hydrocracking reactor 130 of the hydrocracking unit 101 enabled production of 24.7 g of valuable $C_6$-$C_8$ aromatics in a reformer unit with production of only 7.5 g of lighter hydrocarbons. Unlike typical blending of the heavy aromatics column bottoms stream 184 in a fuel oil pool, the current scheme maximizes the recovery of aromatics from the heavy aromatics column bottoms stream 184 in the second stage hydrocracking reactor 130 of the hydrocracking unit 101 as shown in the Table.

SPECIFIC EMBODIMENTS

While the following is described in conjunction with specific embodiments, it will be understood that this description is intended to illustrate and not limit the scope of the preceding description and the appended claims.

A first embodiment of the invention is an integrated process for maximizing recovery of aromatics, comprising passing at least a portion of a xylene column bottoms stream to a heavy aromatics column to provide a heavy aromatics column bottoms stream comprising $C_{9+}$ aromatics and a heavy aromatics column overhead stream; and hydrocracking the heavy aromatics column bottoms stream in a second stage hydrocracking reactor of a two-stage hydrocracking reactor in the presence of a hydrocracking catalyst and hydrogen to provide a hydrocracked effluent stream. An embodiment of the invention is one, any or all of prior embodiments in this paragraph up through the first embodiment in this paragraph further comprising hydrocracking a hydrocarbonaceous feed in a first stage hydrocracking reactor in the presence of a first stage hydrocracking catalyst and hydrogen to provide a first stage hydrocracked effluent stream; separating the first stage hydrocracked effluent stream in a fractionation column to provide an overhead stream and a bottoms stream comprising unconverted oil; hydrocracking the bottoms stream comprising unconverted oil and the heavy aromatics column bottoms stream in the second stage hydrocracking reactor in the presence of a second stage hydrocracking catalyst and hydrogen to provide a second stage hydrocracked effluent stream; and passing the second stage hydrocracked effluent stream to the fractionation column. An embodiment of the invention is one, any or all of prior embodiments in this paragraph up through the first embodiment in this paragraph further comprising combining the heavy aromatics column bottoms stream with the bottoms stream comprising unconverted oil to provide a combined stream; and passing the combined stream to the second stage hydrocracking reactor. An embodiment of the invention is one, any or all of prior embodiments in this paragraph up through the first embodiment in this paragraph, wherein each stage of the two-stage hydrocracking reactor comprises one or more beds adaptable to contain the hydrocracking catalyst. An embodiment of the invention is one, any or all of prior embodiments in this paragraph up through the first embodiment in this paragraph further comprising passing the heavy aromatics column bottoms stream in between the one or more beds of the hydrocracking catalyst. An embodiment of the invention is one, any or all of prior embodiments in this paragraph up through the first embodiment in this paragraph further comprising reforming a naphtha feed stream and a heavy naphtha stream taken from the fractionation column in a reforming unit in the presence of hydrogen and a reforming catalyst to provide a reformate effluent stream; passing the reformate effluent stream to a reformate splitter to provide a reformate splitter overhead stream comprising $C_{7-}$ hydrocarbons and a reformate splitter bottoms stream comprising $C_{8+}$ aromatics; and passing the reformate splitter bottoms stream to a xylene column to provide a xylene column overhead stream comprising a mixture of xylenes and the xylene column bottoms stream. An embodiment of the invention is one, any or all of prior embodiments in this paragraph up through the first embodiment in this paragraph further comprising passing the reformate splitter overhead stream to an extraction unit to provide a benzene rich extract stream; passing the benzene rich extract stream and a transalkylated effluent stream to a benzene column to recover benzene in an overhead stream and provide a benzene column bottoms stream; passing the benzene column bottoms stream to a toluene column to provide a toluene rich overhead stream and a toluene column bottoms stream; passing the toluene rich overhead stream and the heavy aromatics column overhead stream to a transalkylation unit comprising transalkylation catalyst to produce the transalkylated effluent stream; and passing the toluene column bottoms stream to the xylene column. An embodiment of the invention is one, any or all of prior embodiments in this paragraph up through the first embodiment in this paragraph further comprising passing the xylene column overhead stream to a paraxylene separation unit to separate paraxylene and provide a paraxylene lean stream; passing the paraxylene lean stream to an isomerization unit to provide an isomerized effluent stream; and passing the isomerized effluent stream to the xylene column. An embodiment of the invention is one, any or all of prior embodiments in this paragraph up through the first embodiment in this paragraph further comprising passing the xylene column bottoms stream to an ortho-xylene column to recover ortho-xylene in an overhead stream and provide an ortho-xylene column bottoms stream; and passing the ortho-xylene column bottoms stream to the heavy aromatics column to provide the heavy aromatics column bottoms stream. An embodiment of the invention is one, any or all of prior embodiments in this paragraph up through the first embodiment in this paragraph, wherein the stream to the xylene column comprises one or more of the reformate splitter bottoms stream, the toluene column bottoms stream, and the isomerized effluent stream. An embodiment of the invention is one, any or all of prior embodiments in this paragraph up through the first embodiment in this paragraph further comprising at least one of sensing at least one parameter of the integrated process for maximizing recovery of aromatics and generating a signal or data from the sensing; generating and transmitting a signal; or generating and transmitting data.

A second embodiment of the invention is an integrated process for maximizing recovery of aromatics, comprising passing a stream to a xylene column to provide a xylene column overhead stream comprising a mixture of xylenes and a xylene column bottoms; passing at least a portion of the xylene column bottoms stream to a heavy aromatics column to provide a heavy aromatics column bottoms stream comprising $C_{9+}$ aromatics and a heavy aromatics column overhead stream; and hydrocracking the heavy aromatics column bottoms stream and an unconverted oil stream in a second stage hydrocracking reactor of a two-stage hydrocracking reactor to provide a second stage hydrocracked effluent stream. An embodiment of the invention is one, any or all of prior embodiments in this paragraph up through the second embodiment in this paragraph further comprising hydrocracking a hydrocarbonaceous feed in a first stage hydrocracking reactor in the presence of the hydrocracking catalyst and hydrogen to provide a first stage hydrocracked effluent stream; combining the second stage hydrocracked effluent stream with the first stage hydrocracked effluent stream to provide a combined hydrocracked effluent stream; and fractionating the combined hydrocracked effluent stream in a fractionation column to provide an overhead stream and the unconverted oil stream. An embodiment of the invention is one, any or all of prior embodiments in this paragraph up through the second embodiment in this paragraph further comprising passing the xylene column overhead stream to a paraxylene separation unit to separate paraxylene and provide a paraxylene lean stream; and passing the paraxylene lean stream to an isomerization unit to provide an isomerized effluent stream; and passing the isomerized effluent stream to the xylene column. An embodiment of the invention is one, any or all of prior embodiments in this paragraph up through the second embodiment in this paragraph further comprising reforming a naphtha feed stream and a heavy naphtha stream taken from the fractionation column in a reforming unit in the presence of hydrogen and a reforming catalyst to provide a reformate effluent stream; and passing the reformate effluent stream to a reformate splitter to provide a reformate splitter overhead stream comprising $C_{7-}$ hydrocarbons and a reformate splitter bottoms stream comprising $C_{8+}$ aromatics; and passing the reformate splitter bottoms stream to the xylene column. An embodiment of the invention is one, any or all of prior embodiments in this paragraph up through the second embodiment in this paragraph further comprising passing the reformate splitter overhead stream to an extraction unit to provide a benzene rich extract stream; passing the benzene rich extract stream and a transalkylated effluent stream to a benzene column to recover benzene in an overhead stream and provide a benzene column bottoms stream; passing the benzene column bottoms stream to a toluene column to provide a toluene rich overhead stream and a toluene column bottoms stream; passing the toluene rich overhead stream and the heavy aromatics column overhead stream to a transalkylation unit comprising transalkylation catalyst to produce the transalkylated effluent stream; and passing the toluene column bottoms stream to the xylene column. An embodiment of the invention is one, any or all of prior embodiments in this paragraph up through the second embodiment in this paragraph, wherein each stage of the two-stage hydrocracking unit comprises one or more beds adaptable to contain a hydrocracking catalyst. An embodiment of the invention is one, any or all of prior embodiments in this paragraph up through the second embodiment in this paragraph further comprising passing the heavy aromatics column bottoms stream in between the one or more beds of the hydrocracking catalyst.

A third embodiment of the invention is an integrated process for maximizing recovery of aromatics, comprising passing a stream to a xylene column to provide a xylene column overhead stream comprising a mixture of xylenes and a xylene column bottoms stream; passing the xylene column overhead stream to a paraxylene separation unit to separate paraxylene and provide a paraxylene lean stream; passing at least a portion of the xylene column bottoms stream to a heavy aromatics column to provide a heavy aromatics column bottoms stream comprising $C_{9+}$ aromatics; and hydrocracking the heavy aromatics column bottoms stream in a second stage hydrocracking reactor of a two-stage hydrocracking reactor in the presence of a hydrocracking catalyst and hydrogen to provide an overhead stream comprising $C_{6-}$ hydrocarbons and a heavy naphtha stream. An embodiment of the invention is one, any or all of prior embodiments in this paragraph up through the third embodiment in this paragraph further comprising hydrocracking a hydrocarbonaceous feed in a first stage hydrocracking reactor in the presence of a first stage hydrocracking catalyst and hydrogen to provide a first stage hydrocracked effluent stream; fractionating the first stage hydrocracked effluent stream in a fractionation column to provide the overhead stream and a bottoms stream comprising unconverted oil; hydrocracking the heavy aromatics column bottoms stream and the bottoms stream comprising unconverted oil in the second stage hydrocracking reactor to provide a second stage hydrocracked effluent stream; and passing the second stage hydrocracked effluent stream to the fractionation column.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. An integrated process for maximizing recovery of aromatics, comprising:
    passing at least a portion of a xylene column bottoms stream to a heavy aromatics column to provide a heavy aromatics column bottoms stream comprising $C_{9+}$ aromatics and a heavy aromatics column overhead stream; and
    hydrocracking the heavy aromatics column bottoms stream in a second stage hydrocracking reactor of a two-stage hydrocracking reactor in the presence of a hydrocracking catalyst and hydrogen to provide a hydrocracked effluent stream.

2. The process of claim 1 further comprising:
    hydrocracking a hydrocarbonaceous feed in a first stage hydrocracking reactor in the presence of a first stage hydrocracking catalyst and hydrogen to provide a first stage hydrocracked effluent stream;
    separating the first stage hydrocracked effluent stream in a fractionation column to provide an overhead stream and a bottoms stream comprising unconverted oil;
    hydrocracking the bottoms stream comprising unconverted oil and the heavy aromatics column bottoms stream in the second stage hydrocracking reactor in the presence of a second stage hydrocracking catalyst and hydrogen to provide a second stage hydrocracked effluent stream; and
    passing the second stage hydrocracked effluent stream to the fractionation column.

3. The process of claim 2 further comprising:
    combining the heavy aromatics column bottoms stream with the bottoms stream comprising unconverted oil to provide a combined stream; and
    passing the combined stream to the second stage hydrocracking reactor.

4. The process of claim 1, wherein each stage of the two-stage hydrocracking reactor comprises one or more beds adaptable to contain the hydrocracking catalyst.

5. The process of claim 4 further comprising passing the heavy aromatics column bottoms stream in between the one or more beds of the hydrocracking catalyst.

6. The process of claim 2 further comprising:
    reforming a naphtha feed stream and a heavy naphtha stream taken from the fractionation column in a reforming unit in the presence of hydrogen and a reforming catalyst to provide a reformate effluent stream;
    passing the reformate effluent stream to a reformate splitter to provide a reformate splitter overhead stream comprising $C_{7-}$ hydrocarbons and a reformate splitter bottoms stream comprising $C_{8+}$ aromatics; and
    passing the reformate splitter bottoms stream to a xylene column to provide a xylene column overhead stream comprising a mixture of xylenes and the xylene column bottoms stream.

7. The process of claim 6 further comprising:
    passing the reformate splitter overhead stream to an extraction unit to provide a benzene rich extract stream;
    passing the benzene rich extract stream and a transalkylated effluent stream to a benzene column to recover benzene in an overhead stream and provide a benzene column bottoms stream;
    passing the benzene column bottoms stream to a toluene column to provide a toluene rich overhead stream and a toluene column bottoms stream;
    passing the toluene rich overhead stream and a heavy aromatics column overhead stream to a transalkylation unit comprising transalkylation catalyst to produce the transalkylated effluent stream; and
    passing the toluene column bottoms stream to the xylene column.

8. The process of claim 6 further comprising:
    passing the xylene column overhead stream to a paraxylene separation unit to separate paraxylene and provide a paraxylene lean stream;
    passing the paraxylene lean stream to an isomerization unit to provide an isomerized effluent stream; and
    passing the isomerized effluent stream to the xylene column.

9. The process of claim 1 further comprising:
passing the xylene column bottoms stream to an ortho-xylene column to recover ortho-xylene in an overhead stream and provide an ortho-xylene column bottoms stream; and
passing the ortho-xylene column bottoms stream to the heavy aromatics column to provide the heavy aromatics column bottoms stream.

10. The process of claim 1, wherein the stream to the xylene column comprises one or more of a reformate splitter bottoms stream, a toluene column bottoms stream, and an isomerized effluent stream.

11. The process of claim 1 further comprising at least one of:
sensing at least one parameter of the integrated process for maximizing recovery of aromatics and generating a signal or data from the sensing;
generating and transmitting a signal; or
generating and transmitting data.

12. An integrated process for maximizing recovery of aromatics, comprising:
passing a stream to a xylene column to provide a xylene column overhead stream comprising a mixture of xylenes and a xylene column bottoms;
passing at least a portion of the xylene column bottoms stream to a heavy aromatics column to provide a heavy aromatics column bottoms stream comprising $C_{9+}$ aromatics and a heavy aromatics column overhead stream; and
hydrocracking the heavy aromatics column bottoms stream and an unconverted oil stream in a second stage hydrocracking reactor of a two-stage hydrocracking reactor to provide a second stage hydrocracked effluent stream.

13. The process of claim 12 further comprising:
hydrocracking a hydrocarbonaceous feed in a first stage hydrocracking reactor in the presence of the hydrocracking catalyst and hydrogen to provide a first stage hydrocracked effluent stream;
combining the second stage hydrocracked effluent stream with the first stage hydrocracked effluent stream to provide a combined hydrocracked effluent stream; and
fractionating the combined hydrocracked effluent stream in a fractionation column to provide an overhead stream and the unconverted oil stream.

14. The process of claim 12 further comprising:
passing the xylene column overhead stream to a paraxylene separation unit to separate paraxylene and provide a paraxylene lean stream; and
passing the paraxylene lean stream to an isomerization unit to provide an isomerized effluent stream; and
passing the isomerized effluent stream to the xylene column.

15. The process of claim 13 further comprising:
reforming a naphtha feed stream and a heavy naphtha stream taken from the fractionation column in a reforming unit in the presence of hydrogen and a reforming catalyst to provide a reformate effluent stream; and
passing the reformate effluent stream to a reformate splitter to provide a reformate splitter overhead stream comprising $C_{7-}$ hydrocarbons and a reformate splitter bottoms stream comprising $C_{8+}$ aromatics; and
passing the reformate splitter bottoms stream to the xylene column.

16. The process of claim 15 further comprising:
passing the reformate splitter overhead stream to an extraction unit to provide a benzene rich extract stream;
passing the benzene rich extract stream and a transalkylated effluent stream to a benzene column to recover benzene in an overhead stream and provide a benzene column bottoms stream;
passing the benzene column bottoms stream to a toluene column to provide a toluene rich overhead stream and a toluene column bottoms stream;
passing the toluene rich overhead stream and the heavy aromatics column overhead stream to a transalkylation unit comprising transalkylation catalyst to produce the transalkylated effluent stream; and
passing the toluene column bottoms stream to the xylene column.

17. The process of claim 12, wherein each stage of the two-stage hydrocracking unit comprises one or more beds adaptable to contain a hydrocracking catalyst.

18. The process of claim 17 further comprising passing the heavy aromatics column bottoms stream in between the one or more beds of the hydrocracking catalyst.

19. An integrated process for maximizing recovery of aromatics, comprising:
passing a stream to a xylene column to provide a xylene column overhead stream comprising a mixture of xylenes and a xylene column bottoms stream;
passing the xylene column overhead stream to a paraxylene separation unit to separate paraxylene and provide a paraxylene lean stream;
passing at least a portion of the xylene column bottoms stream to a heavy aromatics column to provide a heavy aromatics column bottoms stream comprising $C_{9+}$ aromatics; and
hydrocracking the heavy aromatics column bottoms stream in a second stage hydrocracking reactor of a two-stage hydrocracking reactor in the presence of a hydrocracking catalyst and hydrogen to provide a second stage hydrocracked effluent stream.

20. The process of claim 19 further comprising:
hydrocracking a hydrocarbonaceous feed in a first stage hydrocracking reactor in the presence of a first stage hydrocracking catalyst and hydrogen to provide a first stage hydrocracked effluent stream;
fractionating the first stage hydrocracked effluent stream in a fractionation column to provide an overhead stream and a bottoms stream comprising unconverted oil;
hydrocracking the heavy aromatics column bottoms stream and the bottoms stream comprising unconverted oil in the second stage hydrocracking reactor to provide the second stage hydrocracked effluent stream; and
passing the second stage hydrocracked effluent stream to the fractionation column to provide a receiver overhead vapor stream comprising $C_{6-}$ hydrocarbons and a heavy naphtha stream.

* * * * *